United States Patent [19]

Dorn

[11] 4,275,079

[45] Jun. 23, 1981

[54] FUNGICIDAL N-ALKYNYLANILIDES

[75] Inventor: Franz Dorn, Dielsdorf, Switzerland

[73] Assignee: Hoffmann-La Roche Inc., Nutley, N.J.

[21] Appl. No.: 147,676

[22] Filed: May 7, 1980

[30] Foreign Application Priority Data

May 18, 1979 [CH] Switzerland ......................... 4675/79
Mar. 14, 1980 [CH] Switzerland ......................... 2015/80

[51] Int. Cl.$^3$ ...................... C07C 103/58; A01N 9/12; A01N 9/20

[52] U.S. Cl. .................................... 424/324; 564/202; 564/207

[58] Field of Search ................. 564/202, 207; 424/324

[56] References Cited

U.S. PATENT DOCUMENTS 4,151,295 4/1979 Hubele ............................ 424/324 X

*Primary Examiner*—Thomas A. Waltz
*Attorney, Agent, or Firm*—Jon S. Saxe; George M. Gould; William M. Farley

[57] ABSTRACT

N-alkynylanilides, a process for their preparation, fungicidal compositions containing the N-alkynylanilides as the active ingredient and methods for the use of such compounds or compositions for combatting plant fungi are disclosed.

22 Claims, No Drawings

FUNGICIDAL N-ALKYNYLANILIDES

SUMMARY OF THE INVENTION

This invention relates to N-alkynylanilides of the formula

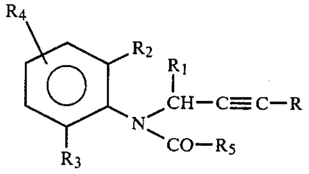

I wherein R is hydrogen, methyl or ethyl, $R_1$ is hydrogen or methyl, $R_2$ and $R_3$ each are an alkyl of from 1 to 3 carbon atoms, alkoxy of from 1 to 3 carbon atoms or halogen, $R_4$ is hydrogen, alkyl of from 1 to 3 carbon atoms or halogen and $R_5$ is the group $—CH_2—O—R_6$ or $—CH_2—S—R_6$ in which $R_6$ is alkenyl of 3 or 4 carbon atoms, or alkynyl of 3 or 4 carbon atoms with the proviso that the total number of carbon atoms in substituents $R_2$, $R_3$ and $R_4$ does not exceed 6.

This invention also relates to a process for the preparation of such compounds, to fungicidal compositions containing these compounds as the active ingredient and to methods for the use of such compounds or compositions in combatting plant fungi.

DETAILED DESCRIPTION OF THE INVENTION

The N-alkynylanilides of this invention are compounds of the formula

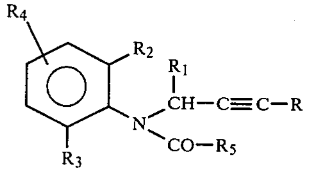

I wherein R is hydrogen, methyl or ethyl, $R_1$ is hydrogen or methyl, $R_2$ and $R_3$ each are alkyl of from 1 to 3 carbon atoms, alkoxy of from 1 to 3 carbon atoms or halogen, $R_4$ is hydrogen, alkyl of from 1 to 3 carbon atoms or halogen and $R_5$ is the group $—CH_2—O—R_6$ or $—CH_2—S—R_6$ in which $R_6$ is alkenyl of 3 or 4 carbon atoms or alkynyl of 3 or 4 carbon atoms, with the proviso that the total number of carbon atoms in substituents $R_2$, $R_3$ and $R_4$ does not exceed 6.

The compounds of formula I possess fungicidal properties and are suitable as fungicidal agents.

The invention is also directed to a process for the preparation of the compounds of formula I, to fungicidal compositions which contain at least one compound of formula I as the active ingredient and to methods for the use of such fungicidal compositions for combatting plant fungi.

In formula I, the alkyl or the alkyl moiety of the alkoxy can be methyl, ethyl, n-propyl or isopropyl.

The term "halogen" includes fluorine, chlorine, bromine or iodine.

When $R_2$ or $R_3$ is alkyl of from 1 to 3 carbon atoms, the alkyl is, preferably, methyl.

$R_4$ preferably is hydrogen.

The phenyl group in formula I is preferably 2,6-disubstituted and, especially, a 2,6-dimethylphenyl.

R preferably is hydrogen.

$R_1$ preferably is methyl.

Compounds of formula I wherein $R_5$ is $—CH_2—O—R_6$ are also preferred. $R_6$ is, preferably, allyl or propargyl.

Especially preferred compounds of formula I are:

2-(Allyloxy)-N-(1-methyl-2-propynyl)-2',6'-acetoxylidide and

N-(1-methyl-2-propynyl)-2-(2-propynyloxy)-2',6'-acetoxylidide.

Since the compounds of formula I can contain asymmetric carbon atoms they can exist as optical antipodes. Independently of this optical isomerism, an atropic isomerism can also be present. In addition, as a consequence of the double bond which is present in the compounds of formula I wherein $R_6$ of $—CH_2—O—R_6$ or $—CH_2—S—R_6$ is alkenyl, geometric isomerism can occur in these compounds. Formula I is, accordingly, intended to include all of these possible isomeric forms.

The process for the preparation of compounds of formula I comprises reacting a compound of the formula

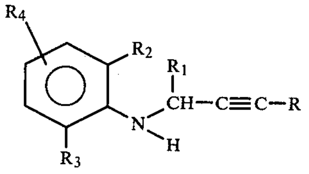

II wherein R, $R_1$, $R_2$, $R_3$ and $R_4$ have the significance given earlier, with a carboxylic acid of the formula $$HO—CO—R_5 \qquad III$$

wherein $R_5$ has the significance given earlier, or with a reactive acid halide, acid anhydride, ester or amide of formula III and, preferably, with the halide or anhydride.

Among the acid halides, the acid chlorides and the acid bromides are preferred.

The reaction is carried out either with or without solvents or diluents which are inert to the reactants. Suitable solvents include aliphatic and aromatic hydrocarbons such as benzene, toluene, xylenes and petroleum ethers, halogenated hydrocarbons such as chlorobenzenes, methylene chloride, ethylene chloride and chloroform, ethers and ether-like compounds such as dialkyl ethers, dioxan and tetrahydrofuran, nitriles such as acetonitrile, N,N-dialkylated amides such as dimethylformamide, dimethyl sulphoxide, ketones such as methyl ethyl ketone and mixtures of such solvents.

The reaction is carried out at a temperature between 0° C. and 180° C. and, preferably, between 20° C. and 120° C. It is often advantageous to carry out the reaction in the presence of an acid-binding agent or condensation agent. Examples of such agents are tertiary amines such as trialkylamines (e.g. triethylamine), pyridine and pyridine bases, and inorganic bases such as the oxides, hydroxides, hydrogen carbonates and carbonates of alkali metals and alkaline earth metals as well as sodium acetate. Moreover, an excess of the compound of formula II can serve as the acid-binding agent.

Compounds of formula II can be prepared by the following reaction scheme:

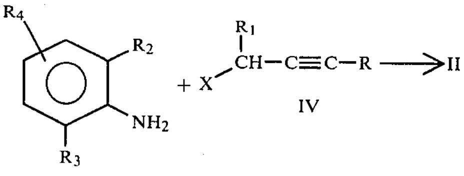

IV

V

The substituent X in formula IV is chlorine, bromine, tosyloxy or mesyloxy group, while the substituents R, $R_1$, $R_2$, $R_3$ and $R_4$ in formulas IV and V have the significance given earlier.

The reaction of a compound of formula IV with a compound of formula V is carried out either with or without solvents or diluents which are inert to the reactants. Suitable solvents or diluents include, for example, those listed above for the reaction of a compound of formula II with a compound of formula III.

Reaction of a compound of formula IV with a compound of formula V is carried out at a temperature between 0° C. and 180° C. and, preferably, between 20° C. and 120° C. It is often advantageous to carry out the reaction in the presence of an acid-binding agent or condensation agent. Preferred agents are inorganic bases such as the oxides, hydroxides, hydrogen carbonates and carbonates of alkali metals and alkaline earth metals as well as sodium acetate. Moreover, an excess of the compound of formula V can serve as the acid-binding agent.

Compounds of formula II in which R is methyl or ethyl are also prepared by alkylating a compound of formula II wherein R is hydrogen according to the following reaction scheme:

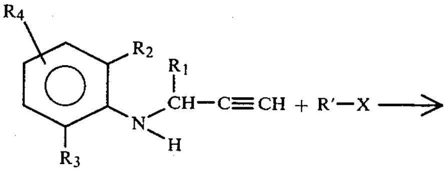

II (R = H)

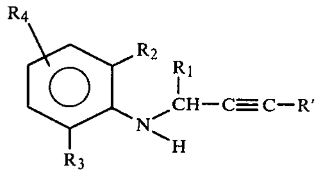

II' wherein R' is methyl or ethyl, X is chlorine, bromine, iodine, tosyloxy or mesyloxy and $R_1$, $R_2$, $R_3$ and $R_4$ have the significance given earlier.

the reaction is carried out in the presence of a base (e.g. an alkali metal amide such as lithium diisopropylamide) in an inert solvent (e.g. a hydrocarbon such as benzene or an ether such as diethyl ether or tetrahydrofuran) and at a temperature between-70° C. and room temperature. Alkyl halides, especially bromides and iodides are the preferred alkylating agents.

Compounds of formulas III, IV and V are either known or can readily be prepared according to methods known per se.

If no planned synthesis for the isolation of pure isomers is carried out, a compound of formula I, prepared as described above, normally results as a mixture of two or more isomers. However, the isomers can be isolated according to known methods, if desired.

The compounds of formula I have a specific fungicidal action on plants which are attacked by fungi. Examples of such plants which are protected by the compounds of formula I include maize, vegetables, sugar beet, soya, ground nut, fruit trees, ornamental plants and, especially, vines, hops, cucumber plants (cucumbers, pumpkins and melons), Solanaceae (e.g. potatoes, tobacco and tomatoes) and banana, pineapple, avocado, cocoa and natural rubber plants.

Further, the compounds of formula I are also active against eggs of, for example, Arachnida and insects as well as against Arachnida and insects themselves. They are accordingly also suitable for use as the active ingredient in insecticidal and acaricidal compositions.

The fungi which appear on plants or parts of plants (fruits, flowers, foliage, stems, tubers or roots) of the aforementioned species and related species can be halted or eliminated by means of the compounds of formula I. Further, parts of plants which grow later remain immune to such fungi.

The compounds of formula I are active against phytopathogenic fungi belonging to the following classes: Basidiomycetes such as rust fungi and, especially, Phycomycetes, particularly the genera Phytophthora, Peronospora, Pseudoperonospora, Pythium, Bremia and Plasmopara belonging to the class of Oomycetes.

The compounds of formula I also have systemic activity. Further, they can be employed as dressings for the treatment of seeds (fruits, tubers and grain) and plant cuttings for protection from fungal infections as well as against phytopathogenic fungi appearing in the soil.

The compounds of formula I are active under greenhouse conditions at a concentration of 5 mg to 500 mg of active ingredient (i.e. compound of formula I) per liter of spray liquor. In the open air, they are advantageously applied in concentrations of 100 g to 2500 g of active ingredient per hectare and treatment. For example, to successfully combat vine mildew, concentrations of 200 g to 1000 g, preferably 200 g to 600 g, of active ingredient per hectare and application are used. To combat cereal rust, concentrations of 500 g to 2500 g, especially, preferably with regard to the most active representatives, 500 to 2000 g of active ingredient per hectare and application are used.

Some of the compounds of formula I possess high systemic activity. Thus, by secondary distribution of the active ingredient (gas phase action), untreated parts of plants can also be protected.

For all practical purposes the compounds of formula I can be classified as largely nontoxic for vertebrates. Individual compounds show $LD_{50}$-values in mice between 400 mg and 1000 mg per kg body weight, while other compounds show $LD_{50}$-values which lie between 1000 mg and 10,000 mg per kg body weight in acute toxicity tests in mice.

This invention is also directed to plant fungicidal compositions comprising compatible carrier material and, as the active ingredient, one or more of the compounds of formula I. These compositions can be, for example, spray liquors, aqueous suspensions, emulsions, emulsifiable concentrates and pulverous preparations. Depending on its type, a plant fungicidal composition of this invention contains from about 0.0001 percent to about 95 percent by weight, based on the weight of the total composition, of a compound or compounds of formula I as the active ingredient.

Examples of compatible carrier material include pulverous materials such as, for example, kaolin, bentonite, talc, whiting, magnesium carbonate and siliceous earth.

For the preparation of pulverous compositions, inert pulverous carrier material, such as kaolin, bentonite, talc, whiting, magnesium carbonate and siliceous earth, can be admixed with the active ingredients (e.g. by grinding them together). In an alternate procedure, the inert pulverous carrier materials can be impregnated with a solution of the active ingredient with the solvent subsequently removed by evaporation, heating or aspiration under reduced pressure.

These powder compositions can be applied to plants to be protected in the form of dusts using standard dusting apparatus. By the addition of wetting and/or dispersing agents to the powdery compositions, the compositions are readily wettable with water and, thus, can be used as aqueous suspensions suitable for spray applications.

To prepare emulsifiable concentrates, the active ingredients can be mixed with an emulsifying agent or dissolved in an inert solvent and mixed with an emulsifier. Ready-for-use emulsions are prepared by dilution of such concentrates with water. These concentrates can contain from about 10 percent to about 95 percent by weight, based on the total weight of the concentrate, of active ingredient.

The fungicidal compositions of this invention can contain, in addition to the compounds of formula I, other active ingredients (e.g. fungicidal agents, insecticidal and acaricidal agents, plant growth regulators, fertilizers and the like). Such combination compositions are useful either for broadening the spectrum of activity or for specifically influencing plant growth (e.g. by reducing the susceptibility towards Oidium and Botrytis species in vine growing). The compositions can be, for example, pulverous compositions or spray liquids depending on the field of application. Examples of some known active ingredients are listed in the following Table:

| Active Ingredient Class | Representative Compounds |
|---|---|
| Dithiocarbamates | Mancozeb [mixture of [(1,2-ethanediylbis (carbamodithioato))-(2-)] manganese and [(1,2-ethanediylbis-(carbamodithioato))(2-)] zinc] |
| Copper compounds | Basic $CuCl_2$ |
| Bordeaux liquor | |
| Sulfur | |
| Phthalimides | Folpet [N-(trichloromethanesulfenyl)phthalimide] Captafol [3a,4,7,7a-tetrahydro-N-(1,1,2,2-tetrachloroethanesulfenyl)phthalimide] |
| Triphenyltin compounds | Fentin hydroxide (triphenyltin hydroxide) Fentin acetate (triphenyltin acetate) |
| Benzimidazole-2-carbamidic acid methyl ester formers | Benomyl [methyl-2-[1-(butylcarbamoyl)benzimidazolyl]-carbamate] Thiophanate [1,2 -di-(3-ethoxycarbonyl-2-thioureido)-benzene] |
| Dicarboximides | Iprodion [3-(3,5-dichlorophenyl)-1-isopropylcarbamoylhydantoin] Procymidon [N-(3',5'-dichlorophenyl)-1,2-dimethylcyclopropane-1,2-dicarboximide] Vinclozoline [3-(3,5-dichlorophenyl)-5-methyl-5-vinyl-1,3-oxazolidine-2,4-dione] |
| Nitriles | Chlorothalonil (2,4,5,6-tetrachloro-1,3-dicyanobenzene) |
| Phosphoric acid esters | |
| Carbamates | |
| Pyrethroids | |
| Insect growth regulators | |
| Gibberellins | |
| Fertilizers | Based on nitrogen, phosphorus, potassium, calcium and trace elements. |

The following Examples illustrate the invention. Unless otherwise stated, all compounds of formula I, which can occur as racemates or optical isomer, are racemates.

EXAMPLE 1

22.4 g of 1-butyn-3-ol tosylate in 26 g of 2,6-dimethylaniline are stirred at 110° C. for 3 hours. The mixture is then poured into ice-water, extracted with ethyl acetate, dried over sodium sulfate and filtered. The solvent is distilled off to yield N-(1-methyl-2-propynyl)-2,6-xylidine; b.p. 68°-72° C./0.05 Torr; m.p. 32°-33° C.

A solution of 2.32 g of allyloxyacetic acid chloride in 5 ml of chloroform and 20 ml of toluene is treated with 6 g of anhydrous sodium carbonate and stirred at room temperature for 15 minutes. 3 g of the N-(1-methyl-2-propynyl)-2,6-xylidine, dissolved in 10 ml of toluene, are then added with cooling. The mixture is subsequently stirred at room temperature for 18 hours, poured into water and extracted with ethyl acetate. The organic phase is washed successively with 2 N sodium hydroxide and 4 N hydrochloric acid, dried over sodium sulfate, filtered and evaporated. The product is distilled in a bulb-tube to yield 2-allyloxy-N-(1-methyl-2-propynyl)-2',6'-acetoxylidide; b.p. 142° C./0.05 Torr.

In an analogous manner:

N-(1-methyl-2-propynyl)-2-(2-propynyloxy)-2',6'-acetoxylidide, b.p. 145° C./0.05 Torr., is prepared from N-(1-methyl-2-propynyl)-2,6-xylidine and propargyloxyacetic acid chloride.

EXAMPLE 2

This Example illustrates the preparation of an emulsifiable concentrate and a ready-for-use spray liquid (oil/water emulsion).

The first three of the following ingredients are dissolved in the solvent.

| Ingredient | Amount |
|---|---|
| Active ingredient (liquid), a compound of formula I | 750 parts by weight |
| Castor oil - ethylene oxide adduct | 100 parts by weight |
| Calcium dodecylbenzene sulfonate | 25 parts by weight |
| Aromatic solvent (mixture of $C_{10}$-alkylbenzenes) | to 1000 parts by volume |

The components are dissolved in the solvent. The resulting emulsifiable concentrate is added to water to prepare a ready-for-use spray liquid, an emulsion (oil/water) which is stable for hours.

EXAMPLE 3

This Example illustrates the preparation of a spray powder.

The following ingredients are admixed in a mixer, the resulting mixture is ground in an air-jet mill and then remixed.

| Ingredient | Amount (parts by weight) |
|---|---|
| Active ingredient (solid), a compound of formula I | 80 |
| Silicic acid, hydrated | 10 |
| Sodium lauryl sulfate | 1 |
| Sodium lignosulfonate | 2 |
| Kaolin (kaolinite) | 7 |

The resulting spray powder, in which the particle size of the active ingredient is below 10 microns, is easily wet by water and forms a well-suspended dispersion for the treatment of plants.

I claim:

1. A compound of the formula

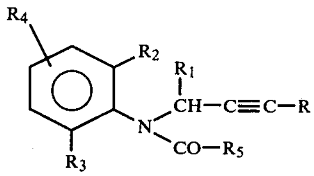

wherein R is hydrogen, methyl or ethyl, $R_1$ is hydrogen or methyl, $R_2$ and $R_3$ each are alkyl of from 1 to 3 carbon atoms, alkoxy of from 1 to 3 carbon atoms or halogen, $R_4$ is hydrogen, alkyl of from 1 to 3 carbon atoms or halogen and $R_5$ is the group $-CH_2-O-R_6$ or $-CH_2-S-R_6$ in which $R_6$ is alkenyl of 3 or 4 carbon atoms or alkynyl of 3 or 4 carbon atoms, with the proviso that the total number of carbon atoms in substituents $R_2$, $R_3$ and $R_4$ does not exceed 6.

2. A compound of claim 1 wherein R is hydrogen.

3. A compound of claim 1 wherein $R_1$ is methyl.

4. A compound of claim 2 wherein $R_1$ is methyl.

5. A compound of claim 1 wherein the substituted phenyl is 2,6-dimethylphenyl.

6. A compound of claim 2 wherein the substituted phenyl is 2,6-dimethylphenyl.

7. A compound of claim 3 wherein the substituted phenyl is 2,6-dimethylphenyl.

8. A compound of claim 1 wherein $R_5$ is $-CH_2-O-R_6$ in which $R_6$ is allyl or propargyl.

9. A compound of claim 2 wherein $R_5$ is $CH_2-O-R_6$ in which $R_6$ is allyl or propargyl.

10. A compound of claim 3 wherein $R_5$ is $CH_2-O-R_6$ in which $R_6$ is allyl or propargyl.

11. A compound of claim 4 wherein $R_5$ is $CH_2-O-R_6$ in which $R_6$ is allyl or propargyl.

12. A compound of claim 5 wherein $R_5$ is $CH_2-O-R_6$ in which $R_6$ is allyl or propargyl.

13. A compound of claim 6 wherein $R_5$ is $CH_2-O-R_6$ in which $R_6$ is allyl or propargyl.

14. A compound of claim 7 wherein $R_5$ is $CH_2-O-R_6$ in which $R_6$ is allyl or propargyl.

15. A compound of claim 1, 2-allyloxy-N-(1-methyl-2-propynyl)-2',6'-acetoxylidide.

16. A compound of claim 1, N-(1-methyl-2-propynyl)-2-(2-propynyloxy)-2',6'-acetoxylidide.

17. A fungicidal composition which comprises compatible carrier material and, as the active ingredient, an amount which is effective as a fungicide of a compound of the formula

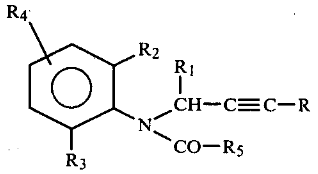

wherein R is hydrogen, methyl or ethyl, $R_1$ is hydrogen or methyl, $R_2$ and $R_3$ each are alkyl of from 1 to 3 carbon atoms, alkoxy of from 1 to 3 carbon atoms or halogen, $R_4$ is hydrogen, alkyl of from 1 to 3 carbon atoms or halogen and $R_5$ is the group $-CH_2-O-R_6$ or $-CH_2-S-R_6$ in which $R_6$ is alkenyl of 3 or 4 carbon atoms or alkynyl of 3 or 4 carbon atoms, with the proviso that the total number of carbon atoms in substituents $R_2$,$R_3$ and $R_4$ does not exceed 6.

18. The fungicidal composition of claim 17 wherein the active ingredient is 2-allyloxy-N-(1-methyl-2-propynyl)-2',6'-acetoxylidide.

19. The fungicidal composition of claim 17 wherein the active ingredient is N-(1-methyl-2-propynyl)-2-(2-propynyloxy)-2',6'-acetoxylidide.

20. A method for combatting plant fungi which comprises treating the plants to be protected with the composition of claim 17.

21. The method of claim 20 wherein the active ingredient is 2-allyloxy-N-(1-methyl-2-propynyl)-2',6'-acetoxylidide.

22. The method of claim 20 wherein the active ingredient is N-(1-methyl-2-propynyl)-2-(2-propynyloxy)-2',6'-acetoxylidide.

* * * * *